United States Patent [19]
Fürsch et al.

[11] Patent Number: 5,928,991
[45] Date of Patent: Jul. 27, 1999

[54] SELECTIVE HERBICIDES BASED ON 1-(2-CHLORO-PHENYL)-4-(N-CYCLOHEXYL-N-ETHYL-AMINOCARBONYL)-1,4-DIHYDRO-5H-TETRAZOL-5-ONE AND PROPANIL

[75] Inventors: Helmut Fürsch, Leichlingen, Germany; Jakob Heeres, Zuidlaren, Netherlands; Toshio Goto, Shimotsuga-gun, Japan

[73] Assignee: Bayer Aktiengesellschaft, Leverkusen, Germany

[21] Appl. No.: 09/007,131

[22] Filed: Jan. 14, 1998

[30] Foreign Application Priority Data

Jan. 21, 1997 [DE] Germany ............................... 19701845

[51] Int. Cl.$^6$ .......................... A01N 25/32; A01N 37/22; A01N 43/713
[52] U.S. Cl. ............................................ 504/103; 504/139
[58] Field of Search ...................... 504/103, 139

[56] References Cited

U.S. PATENT DOCUMENTS

| | | | |
|---|---|---|---|
| 4,868,321 | 9/1989 | Theodoridis | 558/17 |
| 5,362,704 | 11/1994 | Goto et al. | 504/134 |

FOREIGN PATENT DOCUMENTS 0 612 735 A1   8/1994   European Pat. Off. .

*Primary Examiner*—S. Mark Clardy
*Attorney, Agent, or Firm*—Sprung Kramer Schaefer & Briscoe

[57] ABSTRACT

The novel herbicidally active compound combinations comprising (a) 1-(2-chloro-phenyl)-4-(N-cyclohexyl-N-ethyl-aminocarbonyl)-1,4-dihydro-5H-tetrazol-5-one and (b) N-(3,4-dichloro-phenyl)-propanamide (Propanil) exhibit synergistic activity at certain weight ratios and can be employed as selective herbicides in a variety of crops (for example rice and wheat).

5 Claims, No Drawings

SELECTIVE HERBICIDES BASED ON 1-(2-CHLORO-PHENYL)-4-(N-CYCLOHEXYL-N-ETHYL-AMINOCARBONYL)-1,4-DIHYDRO-5H-TETRAZOL-5-ONE AND PROPANIL

The invention relates to novel selective herbicidal, synergistic active compound combinations of the known compound 1-(2-chloro-phenyl)-4-(N-cyclohexyl-N-ethyl-aminocarbonyl)-1,4-dihydro-5H-tetrazol-5-one and the active compound Propanil, which is also known, which can be used particularly successfully for the selective control of weeds in a variety of crop plants.

The compound 1-(2-chloro-phenyl)-4-(N-cyclohexyl-N-ethyl-aminocarbonyl)-1,4-di-hydro-5H-tetrazol-5-one— which can also be referred to as 1-(2-chloro-phenyl)-4-(N-cyclohexyl-N-ethyl-carbamoyl)-5(4H)-tetrazolinone or as 4-(2-chloro-phenyl)-N-cyclohexyl-N-ethyl-4,5-dihydro-5-oxo-1H-tetrazol-1-carboxamide—is known as a herbicidally active substance (cf. EP 612 735 /U.S. Pat. No. 5,362,704). However, the herbicidal activity of this compound on its own is not always entirely satisfactory.

The compound of the common name Propanil—which may also be referred to chemically as N-(3,4-dichloro-phenyl)propanamide or as 3',4'-dichloropropion-anilide—has been known as a herbicidally active compound for a long time and is a component of commercially available products. However, once more the herbicidal activity of this compound on its own is not always entirely satisfactory.

Surprisingly, biological experiments have now shown that novel active compound combinations characterized by (a) an effective level of the compound 1-(2-chloro-phenyl)-4-(N-cyclohexyl-N-ethyl-aminocarbonyl)-1,4-dihydro-5H-tetrazol-5-one of the formula (I)

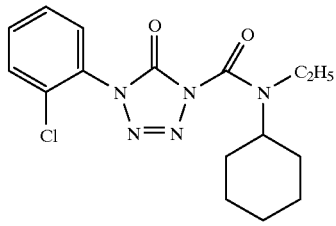

(I)

and (b) an effective level of the compound N-(3,4-dichloro-phenyl)propanamide (Propanil) of the formula (II)

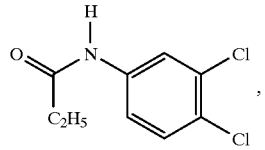

(II)

have pronounced synergistic properties in terms of herbicidal activity and are especially advantageously useful as effective broad range combination products for the selective control of weeds in crop plants such as, for example, rice and wheat, in particular in rice.

Surprisingly, the herbicidal activity of the active compound combination according to the invention is considerably higher than the sum of the activities of the individual active compounds.

This means that an unforeseeable synergistic effect is present, and not merely a complementation of action. The novel active compound combinations are well tolerated by many crops, and even weeds which are otherwise difficult to control are controlled well by the novel active compound combinations. The novel active compound combinations are therefore a useful addition to the range of the selective herbicides.

The active compound combinations according to the invention can be used for example in connection with the following plants:

Dicotyledenous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crop plants of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crop plants of the genera: Oryza, Zea, Triticum, Hordeum, Avena, Secale, Sorghum, Panicum, Saccharum, Ananas, Asparagus and Allium.

However, the use of the active compound combinations according to the invention is in no way restricted to these genera, but also extends in the same manner to other plants.

The synergistic effect of the active compound combinations according to the invention is especially pronounced at specific concentration ratios. However, the weight ratios of the active compounds in the active compound combinations can be varied within relatively wide ranges. In general, 0.01 to 1000 parts by weight, preferably 0.05 to 500 parts by weight, especially preferably 0.1 to 100 parts by weight, of active compound of the formula (II) are used per part by weight of active compound of the formula (I).

The active compounds or active compound combinations can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as auxiliary solvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are:
  for example ammonium salts and ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example ligninsulphite waste liquors and methylcellulose.

Tackifiers such as carboxymethylcellulose and natural and synthetic polymers in the form of powders, granules or latices such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compounds and optionally safener such as, for example, the compound N-(4-methylphenyl)-N'-(1-methyl-1-phenyl-ethyl)-urea (SK-223, dymvon), preferably between 0.5 and 90% of active compounds and optionally safener.

In general, the active compound combinations according to the invention are applied in the form of ready mixes. However, the active compounds in the active compound combinations can also be formulated individually and mixed upon application, that is to say applied in the form of tank mixes.

The novel active compound combinations as such or in the form of their formulations can also be used as mixtures with firther known herbicides, finished formulations or tank mixes again being possible. Mixtures with other known active compounds such as fungicides, insecticides, acaricides, nematicides, bird repellents, growth promoters, plant nutrients and soil conditioners, are also possible. Furthermore, it may be advantageous for specific purposes, in particular when using the post-emergence method, to incorporate mineral or vegetable oils tolerated by plants (for example "Oleo Dupont 11E", which is commercially available) or ammonium salts such as, for example, ammonium sulphate or ammonium thiocyanate, as fuirther additives in the formulations.

The novel active compound combinations can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, dusting or spreading.

The rates of application of the active compound combinations according to the invention can be varied within a certain range; they depend, inter alia, on the weather and on the condition of the soil. In general, the rates of application are between 0.05 and 5 kg per ha, preferably between 0.05 and 2 kg per ha, in particular between 0.1 and 1.0 kg per ha.

The active compound combinations according to the invention can be applied before and after the emergence of the plants, i.e. by the pre-emergence and post-emergence method.

The good herbicidal activity of the novel active compound combinations is evident from the examples below. While the individual active compounds show weaknesses in their herbicidal activity, the combinations all exhibit very efficient control of weeds, and this control exceeds a simple sum of the activities.

In herbicides, a synergistic effect is always present when the herbicidal activity of the active compound combination exceeds that of the active compounds applied individually.

The expected activity for a given combination of two herbicides can be calculated as follows (cf. COLBY, S. R.; "Calculating synergistic and antagonistic responses of herbicide combinations", Weeds 15, pages 20–22, 1967):

If X=% damage by herbicide A (active compound of the formula I) at the rate of application of p kg/ha and Y=% damage by herbicide B (active compound of the formula II) at the rate of application of q kg/ha and E=the expected damage caused by herbicides A and B at a rate of application of p and q kg/ha, then $E=X+Y-(X*Y/100)$.

If the actual damage exceeds the calculated value, the combination is super-additive with regard to its activity, i.e. it shows a synergistic effect.

The examples below reveal that the herbicidal activity of the active compound combinations according to the invention found exceeds the calculated value, i.e. that the novel active compound combinations have a synergistic action.

USE EXAMPLES

To prepare the active compound preparations required for the tests, suitable amounts of a 50% strength water-dispersible powder formulation (50 WP) of the active ingredient of the above formula (I) and a commercially available emulsion concentrate having an active ingredient content of 360 g/l (360 EC) of the active compound of the above formula (II) (Propanil) are weighed out and diluted with water to the desired concentration in question; by mixing, various combinations of the two active ingredient were prepared.

The abbreviations used below have the following meanings:

a.i.=active ingredient;

found=damage or activity found (in percent);

calc.=damage or activity calculated using the COLBY formula above (in percent).

The tests, which were carried out in different geographical regions, were conducted as described below, the observed spread in the results from different countries (the Philippines, Italy, Japan) being due to the very different application conditions in the various regions.

EXAMPLE A

Test in transplanted rice (Philippines)

To prepare a spray preparation, the abovementioned active ingredient preparations are mixed with water. The concentration is adjusted so that the application rate corresponds to 450 l of water/ha.

Rice seedlings (1–2 leaf stage) are transplanted into test plots (2.5 m×2.5 m) in rice paddies (soil saturated with water). 7 days after transplantation, the spray preparation is applied to the test areas (using a hand-operated sprayer). 1 day after the treatment, the soil is flooded to a water depth of 5 cm; the standing water levels are kept constant.

4 weeks after the active compound application, the degree of damage to the rice plants and the herbicidal effect on the emerged weeds Echinochloa crus galli and Monochoria vaginalis is scored visually in percent in comparison to an untreated control.

The figures denote
0%=no action/damage (like untreated control)
100%=total destruction
The results are shown in Table A below.

TABLE A

Test in transplanted paddy rice (Philippines)

| Active ingredient or combination | Application rate (g a.i./ha) | Test plants (Damage or action in %) | | | | Rice (Oryza sp.) found |
|---|---|---|---|---|---|---|
| | | Echinochloa crus galli | | Monochoria vaginalis | | |
| | | found | calc. | found | calc. | |
| (I) (known) | 125 | 99 | | 97 | | 0 |
| (II) (known) | 900 | 93 | | 55 | | 0 |
| (I) + (II) (according to the invention) | 125 + 900 | 100 | (99.9) | 100 | (98.7) | 0 |

EXAMPLE B

Tests in sown rice (Philippines)

To prepare a spray preparation, the abovementioned active ingredient preparations are mixed with water. The concentration is adjusted so that the application rate corresponds to 450 l of water/ha.

Rice seeds are sown in test plots (2.5 m×2.5 m) in rice paddies (soil saturated with water). 7 days after sowing, the spray preparation is applied to the test areas (using a hand-operated sprayer). One day after the treatment, the soil is flooded to a water depth of 5 cm; the standing water levels are kept constant.

4 weeks after the active ingredient application, the degree of damage to the rice plants and the herbicidal effect on the emerged weeds Echinochloa crus galli, Monochoria vaginalis and Sphenoclea zeylanica is scored visually in percent in comparison to an untreated control.

The figures denote:

0%=no action/damage (like untreated control)
100%=total destruction
The results are shown in Tables B1 and B2 below.

TABLE B1

Test in sown rice (Philippines)

| Active ingredient or combination | Application rate (g a.i./ha) | Test plants (Damage or action in %) | | | |
|---|---|---|---|---|---|
| | | Monochoria vaginalis | | Rice (Oryza sp.) | |
| | | found | calc. | found | calc. |
| (I) (known) | 50 | 68 | | 1 | |
| (I) (known) | 900 | | 87 | | 2 |
| (I) + (II) (according to the invention) | 50 + 900 | 98 | (95.8) | 1 | 3 |

TABLE B2

Test in sown rice (Philippines)

| Active ingredient or combination | Application rate (g a.i./ha) | Test plants (Damage or action in %) | | | | | |
|---|---|---|---|---|---|---|---|
| | | Echinochloa crus galli | | Sphenoclea zeylanica | | Rice (Oryza sp.) | |
| | | found | calc. | found | calc. | found | calc. |
| (I) (known) | 50 | 96 | | 62 | | 2 | |
| (II) (known) | 900 | 87 | | 58 | | 3 | |
| (I) + (II) (according to the invention) | 50 + 900 | 100 | (99.5) | 94 | (84) | 3 | 5 |

EXAMPLE C

Test in sown rice (Italy)

To prepare a spray preparation, the abovementioned active ingredient preparations are mixed with water. The concentration is adjusted so that the application rate corresponds to 450 l of water/ha.

Rice seeds are sown in test plots (2 m×5 m) in rice paddies (moist soil). 2 weeks after sowing, the spray preparation is applied to the test areas (using a hand-operated sprayer). 3 days after the treatment, the soil is flooded to a water depth of 5 cm; the standing water levels are kept constant.

4 weeks after the active ingredient application, the degree of damage to the rice plants and the herbicidal effect on the emerged weeds Echinochloa crus galli, Digitaria ascendens, Panicum dichotomiflorum and Polygonum persicaria is scored visually in percent in comparison to an untreated control.

The figures denote:

0%=no action/damage (like untreated control)
100%=total destruction

The results are shown in Tables C1 and C2 below.

TABLE C1

Test in sown rice (Italy)

| Active ingredient or combination | Application rate (g a.i./ha) | Test plants (Damage or action in %) | | |
|---|---|---|---|---|
| | | *Echinochloa crus galli* | | Rice (Oryza sp.) |
| | | found | calc. | found |
| (I) (known) | 300 | 35 | | 0 |
| (II) (known) | 1500 | 45 | | 0 |
| (I) + (II) (according to the invention) | 300 + 1500 | 92 | (64.3) | 0 |

TABLE C2

Test in sown rice (Italy)

| Active ingredient or combination | Application rate (g a.i./ha) | Test plants (Damage or action in %) | | | | | | |
|---|---|---|---|---|---|---|---|---|
| | | *Digitaria ascendens* | | *Panicum dichotomiflorum* | | *Polygonum persicaria* | | Rice (Oryza sp.) |
| | | found | calc. | found | calc. | found | calc. | found |
| (I) (known) | 300 | 70 | | 60 | | 70 | | 0 |
| (II) (known) | 1500 | 75 | | 67 | | 70 | | 0 |
| (I) + (II) (according to invention) | 300 + 1500 | 100 | (92.5) | 92 | (87) | 100 | (91) | 0 |

EXAMPLE D

Test in sown rice (greenhouse, Japan)

To prepare a suitable spray preparation, the abovementioned active ingredient preparations are diluted to the desired concentration by mixing with water.

Vessels for plant cultivation (size: 20 cm×20 cm×9 cm; surface area: 1/2000 Ar) are filled with soil from a rice paddy. Rice seeds and seeds of Echinochloa crus galli are sown into the soil, which is kept moist. At the 1.5–2 leaf stage of rice and Echinochloa crus galli, the dilute active ingredient preparation is applied as a spray (foliar treatment). The active ingredient concentration of the preparation is not important; only the active ingredient application rate per unit area matters.

One day after the treatment, the test vessels are flooded to a water depth of 3 cm. The experiments are subsequently kept flooded (water depth 3 cm).

3 weeks after the active ingredient application, the degree of damage to the plants is scored visually in % damage (or herbicidal effect, respectively) in comparison to an untreated control.

The figures denote:

0%=no action/damage (like untreated control)

100%=total destruction

The results are shown in Tables D1 to D4 below.

TABLE D1

Greenhouse trial (Japan 1996)

| Active ingredient or combination | Application rate (g a.i./ha) | Test plants (Damage or action in %) | | | |
|---|---|---|---|---|---|
| | | *Echinochloa crus galli* | | Rice (Oryza sp.) | |
| | | found | calc. | found | calc. |
| (I) (known) | 50 | 50 | | 5 | |
| (II) (known) | 450 | 10 | | 0 | |
| (I) + (II) (according to the invention) | 50 + 450 | 80 | (55) | 5 | (5) |

TABLE D2

Greenhouse test (Japan 1996)

| Active ingredient or combination | Application rate (g a.i./ha) | Test plants (Damage or action in %) | | | |
|---|---|---|---|---|---|
| | | Echinochloa crus galli | | Rice (Oryza sp.) | |
| | | found | calc. | found | calc. |
| (I) (known) | 100 | 80 | | 10 | |
| (II) (known) | 450 | 10 | | 0 | |
| (I) + (II) (according to the invention) | 100 + 450 | 93 | (82) | 10 | (10) |

TABLE D3

Greenhouse test (Japan 1996)

| Active ingredient or combination | Application rate (g a.i./ha) | Test plants (Damage or action in %) | | | |
|---|---|---|---|---|---|
| | | Echinochloa crus galli | | Rice (Oryza sp.) | |
| | | found | calc. | found | calc. |
| (I) (known) | 50 | 50 | | 5 | |
| (II) (known) | 900 | 50 | | 0 | |
| (I) + (II) (according to the invention) | 50 + 900 | 90 | (75) | 5 | (5) |

TABLE D4

Greenhouse trial (Japan 1996)

| Active ingredient or combination | Application rate (g a.i./ha) | Test plants (Damage or action in %) | | | |
|---|---|---|---|---|---|
| | | Echinochloa crus galli | | Rice (Oryza sp.) | |
| | | found | calc. | found | calc. |
| (I) (known) | 100 | 80 | | 10 | |
| (II) (known) | 900 | 50 | | 0 | |
| (I) + (II) (according to the invention) | 100 + 900 | 100 | (90) | 10 | (10) |

We claim:

1. Selective herbicidal compositions, characterized by a content of an active compound combination comprising (a) 1-(2-chloro-phenyl)-4-(N-cyclohexyl-N-ethyl-aminocarbonyl)-1,4-di-hydro-5H-tetrazol-5-one of the formula (I)

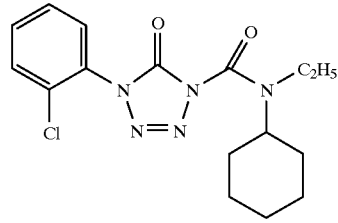

(I)

and (b) N-(3,4-dichloro-phenyl)-propanamide (Propanil) of the formula (II)

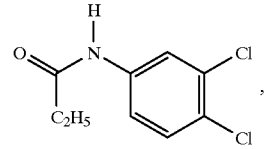

(II)

where 0.01 to 1000 parts by weight of the active compound of the formula (II) are employed per part by weight of the active compound of the formula (I).

2. Selective herbicidal compositions according to claim 1 characterized in that 0.05 to 500 parts by weight of the active compound of formula (II) are employed per part by weight of the active compound of the formula (I) in the active compound combination.

3. Selective herbicidal compositions according to claim 1, characterized in that 0.1 to 100 parts by weight of the active compound of the formula (II) are employed per part by weight of the active compound of the formula (I) in the active compound combination.

4. Selective herbicidal compositions according to claim 1, characterized in that they comprise a safener in addition to the active compound combination.

5. Method for the selective control of barnyard grass, characterized in that an active compound combination according to claim 1 allowed to act on barnyard grass and/or their habitat.

* * * * *